US011990245B2

(12) United States Patent
Sivakumar et al.

(10) Patent No.: US 11,990,245 B2
(45) Date of Patent: May 21, 2024

(54) DYNAMIC INFECTION MAP

(71) Applicant: International Business Machines Corporation, Armonk, NY (US)

(72) Inventors: Gandhi Sivakumar, Bentleigh (AU); Lynn Kwok, Bundoora (AU); Kushal S. Patel, Pune (IN); Sarvesh S. Patel, Pune (IN)

(73) Assignee: International Business Machines Corporation, Armonk, NY (US)

(*) Notice: Subject to any disclaimer, the term of this patent is extended or adjusted under 35 U.S.C. 154(b) by 143 days.

(21) Appl. No.: 17/130,106

(22) Filed: Dec. 22, 2020

(65) Prior Publication Data

US 2022/0199264 A1 Jun. 23, 2022

(51) Int. Cl.
| | | |
|---|---|---|
| *G16H 50/80* | (2018.01) | |
| *G16Y 10/60* | (2020.01) | |
| *G16Y 40/10* | (2020.01) | |
| *H04L 67/125* | (2022.01) | |

(52) U.S. Cl.
CPC ............ *G16H 50/80* (2018.01); *G16Y 10/60* (2020.01); *G16Y 40/10* (2020.01); *H04L 67/125* (2013.01)

(58) Field of Classification Search
None
See application file for complete search history.

(56) References Cited

U.S. PATENT DOCUMENTS

| | | | | |
|---|---|---|---|---|
| 11,504,011 B1* | 11/2022 | Jain | ....................... | A61B 5/1118 |
| 11,570,205 B1* | 1/2023 | Kerr | ..................... | H04W 12/47 |
| 2005/0149358 A1 | 7/2005 | Sacco | | |
| 2010/0238023 A1 | 9/2010 | Kahn | | |
| 2017/0024531 A1 | 1/2017 | Malaviya | | |
| 2018/0168464 A1* | 6/2018 | Barnett, Jr. | .......... | A61B 5/6861 |
| 2019/0333647 A1* | 10/2019 | Hoss | ...................... | G06N 7/01 |
| 2020/0176125 A1* | 6/2020 | Chatterjea | .............. | G16H 40/40 |
| 2021/0151198 A1* | 5/2021 | Sabeti | .................. | H04W 4/023 |
| 2021/0257107 A1* | 8/2021 | Hassan | .................. | G16H 10/60 |
| 2021/0313073 A1* | 10/2021 | McSchooler | .......... | G16H 50/80 |
| 2021/0319894 A1* | 10/2021 | Sobol | ..................... | G16H 40/67 |
| 2021/0398667 A1* | 12/2021 | Fujioka | .................. | G16H 40/67 |
| 2022/0028563 A1* | 1/2022 | Klasson | ................. | G16H 50/20 |
| 2022/0037029 A1* | 2/2022 | Wu | ......................... | G16H 50/50 |
| 2022/0037033 A1* | 2/2022 | Srinivasan | ............. | G06F 16/29 |
| 2022/0122741 A1* | 4/2022 | Mody | ................ | H04W 12/088 |
| 2022/0170756 A1* | 6/2022 | Imtiyaz Shaikh | ...... | H04W 4/44 |

(Continued)

OTHER PUBLICATIONS

Anonymous. "Cognitive Route Determination for Pandemic-Contamination Avoidance." Published Jun. 19, 20. 7 pages. Published by ip.com. https://priorart.ip.com/IPCOM/000262686.

(Continued)

*Primary Examiner* — Chris Parry
*Assistant Examiner* — Abderrahmen Chouat
(74) *Attorney, Agent, or Firm* — Heather Johnston

(57) ABSTRACT

A network architecture may receive situational data. The network architecture may acquire participant data associated with a participant. The network architecture may accept object data associated with an object. The network architecture may generate likelihood of infectiousness of the object based on the participant data and the object data. The network architecture may display the likelihood of infectiousness to one or more users.

17 Claims, 9 Drawing Sheets

(56) References Cited

U.S. PATENT DOCUMENTS

| | | | |
|---|---|---|---|
| 2022/0171412 A1* | 6/2022 | Cui | G05D 1/12 |
| 2022/0199266 A1* | 6/2022 | Achin | G16H 50/20 |

OTHER PUBLICATIONS

Anonymous. "COVID-19 HPC Consortium." Accessed Aug. 17, 20. 2 pages. Published by Xsede. https://www.xsede.org/covid19-hpc-consortium.

Anonymous. "The COVID-19 High Performance Computing Consortium." Accessed Aug. 17, 2020. 8 pages. Published by Covid-19 HPC Consortium. https://covid19-hpc-consortium.org/.

Anonymous. "World experts and funders set priorities for COVID-19 research." Published Feb. 12, 2020. Accessed Aug. 18, 2020. 2 pages. Published by World Health Organization. https://www.who.int/news-room/detail/12-02-2020-world-experts-and-funders-set-priorities-for-covid-19-research.

Boulos, M., et al., "Geographical tracking and mapping of coronavirus disease COVID-19/severe acute respiratory syndrome coronavirus 2 (SARS-CoV-2) epidemic and associated events around the world: how 21st century GIS technologies are supporting the global fight against outbreaks and epidemics." Published Mar. 11, 2020. 12 pages. Published by Springer Nature. https://ij-healthgeographics.biomedcentral.com/articles/10.1186/s12942-020-00202-8.

Cameron, A., "5G, cellular's next step, brings new positioning capabilities." Published Feb. 21, 2018. Accessed Aug. 17, 2020. 4 pages. Published by GPS World. https://www.gpsworld.com/5g-cellulars-next-step-brings-new-positioning-capabilities/.

Etherington, D., "IBM and The Weather Channel launch detailed local COVID-19 maps and data tracking." Published Mar. 25, 20. 1 page. Published by TechCrunch. https://techcrunch.com/2020/03/25/IBM-and-the-weather-channel-launch-detailed-local-covid-19-maps-and-data-tracking/?guccounter=1.

Gunnarsson, F., et al., "LTE Positioning and RTK: Precision down to the centimeter." Published Nov. 9, 2018. Accessed Mar. 17, 2020. 3 pages. Published by Ericsson. https://www.ericsson.com/en/blog/2018/11/lte-positioning-and-rtk-precision-down-to-the-centimeter.

Mell, et al., "The NIST Definition of Cloud Computing," Recommendations of the National Institute of Standards and Technology, U.S. Department of Commerce, Special Publication 800-145, Sep. 2011, 7 pgs.

\* cited by examiner

500

600

✹ HIGH VISIBILITY
⬤ MODERATE VISIBILITY
■ LOW VISIBILITY

DYNAMIC INFECTION MAP

BACKGROUND

The present disclosure relates generally to the field of combatting infection, and more specifically to contact tracing.

Pathogens are often spread by direct or indirect contact between people. The spread of pathogens can thereby be inhibited by harnessing and distributing data, such as known instances of a pathogen, the decay rate of the pathogen, and the viability of the pathogen over time.

SUMMARY

Embodiments of the present disclosure include a system, method, and computer program product for tracking infection.

A network architecture may receive situational data. The network architecture may receive participant data associated with a participant. The network architecture may accept object data associated with an object. The network architecture may generate a likelihood of infectiousness of the object based on the participant data and the object data. The network architecture may display the likelihood of infectiousness to one or more users.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
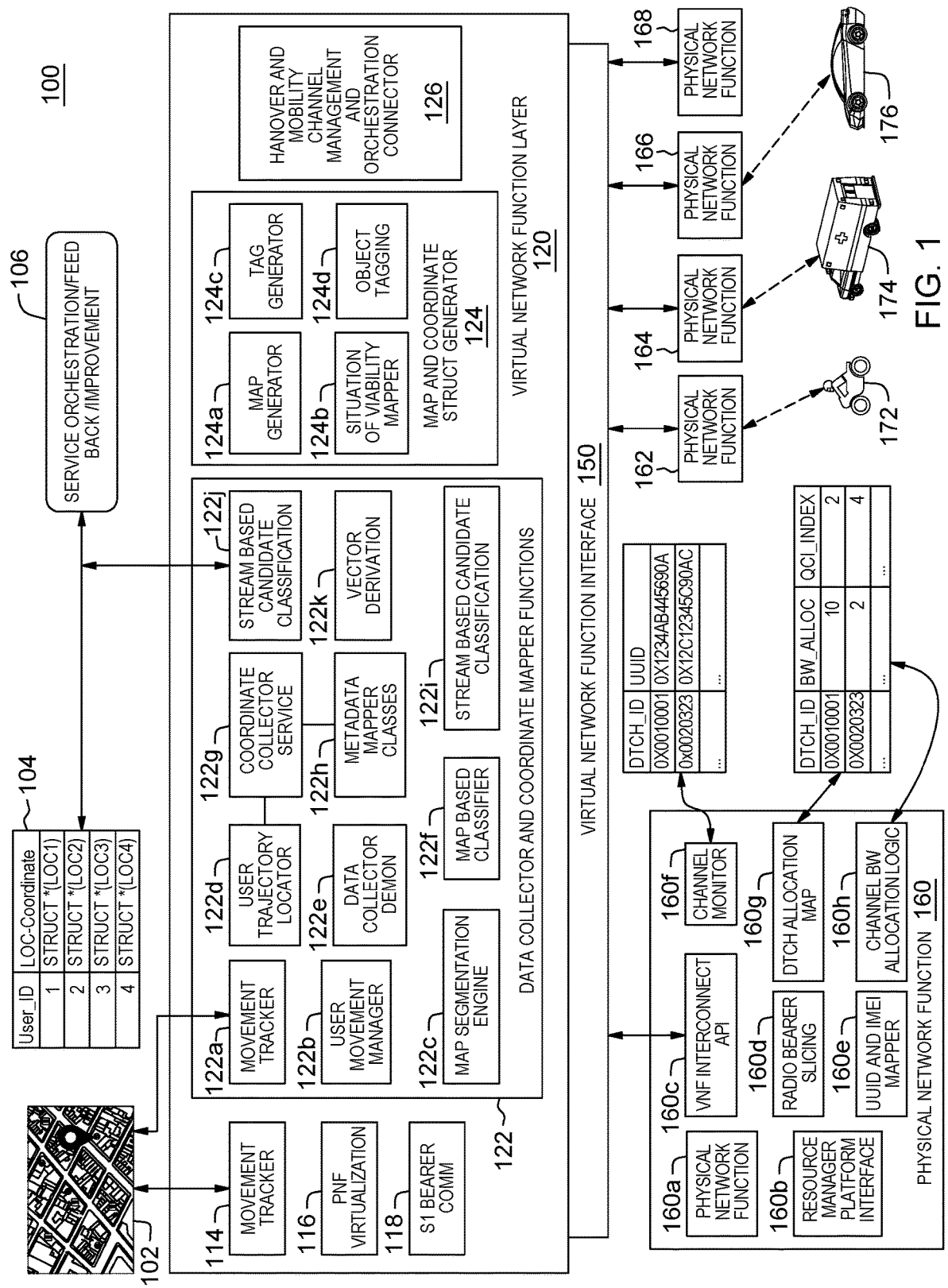
FIG. 1 illustrates a system for tracking infection in accordance with some embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

Aspects of the present disclosure relate generally to the field of combatting infection, and more specifically to contact tracing. It will be readily understood that the instant components, as generally described and illustrated in the figures herein, may be arranged and designed in a wide variety of different configurations. Thus, the following detailed description of the embodiments of at least one of a method, apparatus, non-transitory computer readable medium, and system, as represented in the attached figures, is not intended to limit the scope of the application as claimed but is merely representative of selected embodiments.

The instant features, structures, or characteristics as described throughout this specification may be combined or removed in any suitable manner in one or more embodiments. For example, the usage of the phrases "example embodiments," "some embodiments," or other similar language throughout this specification refers to the fact that a particular feature, structure, or characteristic described in connection with the embodiment may be included in at least one embodiment. Thus, appearances of the phrases "example embodiments," "in some embodiments," "in other embodiments," or other similar language throughout this specification do not necessarily all refer to the same group of embodiments, and the described features, structures, or characteristics may be combined or removed in any suitable manner in one or more embodiments. Further, in the diagrams, any connection between elements can permit one-way and/or two-way communication even if the depicted connection is a one-way or a two-way arrow. Also, any device depicted in the drawings can be a different device. For example, if a mobile device is shown sending information, a wired device can also be used to send the information.

Artificial intelligence (AI) is contributing to technological improvement in a variety of disciplines. Machine learning (ML), for example, has been used to make transportation systems more intelligent, providing transportation agencies, governments, corporations, and private car owners the opportunity to commute, drive, and travel safer: advanced vehicles may now offer features such as automatic emergency braking, lane keep assist, lane change alert, rear vision cameras, parking assist, intelligent headlights, and even self-parking and self-driving options.

Advancements in communications can be capitalized on to customize specific analytics in real time, enabling accurate tracking of various items of interest. A feature of the 5G network is that the 5G network is itself intelligent and cognitive: 5G New Radio (NR) allows for groundbreaking positioning performance by providing large bandwidths which enable precise timing; new frequency bands in the millimeter wave range; massive multiple input, multiple output (MIMO) datastreams for accurate angle of arrival estimations; and new architectural options supporting precision in positioning. Such advancements permits precisely determining device locations while offering the strength necessary for location-specific application development and location-driven customized analytics.

For example, infectious diseases are caused by pathogens: microorganisms (such as bacteria, viruses, parasites, and fungi) which may be spread by person-to-person contact or by an infected person interacting with an object and then another person interacting with the same object in a short span of time. Transmission of such pathogens can be mitigated by providing individuals information about locations of infection so that individuals can avoid infected areas and, thus, prevent themselves from catching the pathogen. Viability data for a pathogen under certain conditions can be used to calculate when it is safe to return to an area that was infected; in other words, information about a pathogen can be used to determine when the pathogen is not likely to be caught because the pathogen is no longer transmissible. This information allows individuals to avoid an infected area and then return to the area when it is likely safe to do so. Additionally, this information can be used to identify which locations or objects would benefit from fumigation to remove a pathogen to prevent it from spreading.

It may be beneficial to describe certain terms relevant to the disclosure.

A pathogen may be a bacterium, virus, microbe, other organism, or other agent that causes, carries, or spreads a condition. A communicable pathogen may be any infectious agent. A condition may be a disease, infection, affliction, or something that otherwise changes the status or state of something.

Viability may be described as the ability to survive or the ability to spread. Viability data is information about life or survivability. Viability of a pathogen, for example, may include the transmissibility of the pathogen, the ability of the pathogen to replicate/procreate, or the ability of the pathogen to infect.

Atmospheric conditions may impact viability. Atmospheric conditions are the conditions of the atmosphere at a specified location and time. Atmospheric conditions may include temperature, humidity, air pressure, air density, precipitation, sunlight, cloud cover, wind, air motion, radiation (such as a UV index), air quality, and similar variables. Atmospheric conditions may be measured at a natural location, such as at a tree in the wilderness in the midst of a large uninhabited area, or in a relatively controlled environment, such as in a parking structure in an urban area, or in a thoroughly controlled environment, such as a climate-controlled room. Atmospheric conditions change over time; for example, a parking spot may be subject to direct sunlight at 35° Celsius at noon and the same parking spot may be subject to zero sun exposure at 25° Celsius twelve hours later.

Viability varies based on various conditions. Typically, the viability of a specific pathogen is identified for specific atmospheric conditions and on a particular type of surface; if a variable changes, the viability of the pathogen may change. For example, the viability of one mole of a virus deposited on copper at 20° Celsius may vary significantly if the temperature is changed to 40° Celsius. Similarly, either scenario may vary significantly from the viability if the same one mole of the virus if it is instead deposited on stainless steel at either 20° Celsius or 40° Celsius.

For example, the 2019 novel coronavirus (2019-nCoV) that causes the 2019 novel coronavirus disease (COVID-19) has been found to be viable for different lengths of time on different surfaces. Under standard atmospheric conditions, some studies have found 2019-nCoV to be viable on various surfaces for different lengths of time: copper for up to four hours, cardboard for up to twenty-four hours, stainless steel for up to two days, and plastic for up to three days. Tracking which surfaces a contagion such as 2019-nCoV has come into contact with and calculating the likelihood of how long the contagion is viable based on this data enables more accurate tracing of likely infection. Such calculations may also minimize the amount of time the potentially infected surfaces are avoided while empowering safe interaction.

The present disclosure discusses the involvement of users and participants. People may opt in to (or opt out of) participating in the present disclosure in various ways. An individual may, for example, decide to not engage in the use of the present disclosure at all, thus effectively opting out of participation; another individual may use features of the present disclosure without submitting information to an online instance of the present disclosure; still another individual may fully use the present disclosure by submitting various information such as location, likelihood of infection, intended route, data collected from vehicles and other internet-of-things (IoT) devices, and other information to a data repository in accordance with the present disclosure. In some embodiments, participating IoT devices may collect data to generate an infection map based on pathogen data, object data, object location, and environmental data.

The present disclosure refers an individual who receives data through the system as a user; a user does not necessarily input data into the system but does use the system. The present disclosure refers to an individual who inputs data into the system as a participant; a participant does not necessarily receive data through the system. A user may be a participant and vice versa; specifically, an individual who both contributes data to the system and receives information from the system may be referred to as both a user and a participant. For clarity, throughout the present disclosure, an individual is defined by the role the individual is actively playing: a person who receives information is called a user, and a person who inputs information is called a participant, even if the same person is performing both actions.

The present disclosure includes a solution for combatting the spread of infection by tracking infection and enabling users to avoid potential infection. Pathogens, such as those that cause infectious diseases, are known to spread disease in various ways such as, for example through contact between an individual carrying a pathogen with another individual, or by passing a pathogen to an object which another individual then encounters. Individuals may be able to decrease the likelihood of obtaining a pathogen, and thereby decrease the likelihood of obtaining and spreading a disease, by avoiding contact with the pathogen while the pathogen is viable. Avoiding contact with a viable pathogen requires knowing where the viable pathogen is. The present disclosure provides a further solution that enables users to identify where a viable pathogen may be such that users may avoid exposure to the pathogen and enabling containment of the disease caused by the pathogen.

The help users identify where a viable pathogen is, the present disclosure provides a means to generate a context-aware dynamic infection map, that indicates infection status of objects, such as vehicles or tables, as well as infection status of participating individuals may be tracked.

FIG. 1 illustrates a system for tracking infection 100 in accordance with some embodiments of the present disclosure. A map 102 may be used to display locations of known, likely, plausible, and possible infection. The map 102 may also be referred to as a display 102 or a map display 102. The map 102 may display a current user location. The map 102 may cover a localized region, such as a city or a borough of a city, or a wider territory, such as a state or a country. The map 102 may cover the intended route of a user and the real time data of potential infection along that route; for example, a user may enable location services on a mobile device and input a destination, and the system may display one or more routes between the user and the destination as well as the current potential infections along the route. The map 102 may display a relatively short route, such as a walking route to a grocery store, or a longer route, such as a trip to visit a relative in a different state. In some embodiments, settings on a map interface may enable a user to automatically reroute a route around infection sites such that a user may opt to avoid sites of known, likely, plausible, or possible infection; a user may set individual radial distance to stay away from the source for each likelihood of infection, or a user may set a common radius for all possible infections or all infections at or above a specified likelihood level, or a radius may be automatically selected by the system.

The display 102 may communicate with various components. The display 102 may communicate with a network architecture layer 120 such as a virtual network function (VNF) layer 120. The VNF layer 120 may include a movement tracker 114 which may track the movement of a user and/or of participants recognized to either be infectious or have recently come into contact with a contagion. A movement tracker 114 may be a dedicated component or embedded in an IoT device such as a mobile phone, keychain key finder, vehicle component, or other IoT gadget. The VNF layer 120 may further include a physical network function 116, also referred to as a PNF virtualization 116. The VNF layer 120 may also include a bearer 118 to transport packets. FIG. 1 shows the bearer as an S1 Bearer Comm 118; other bearers, such as a radio bearer, S5/S8 bearer, or similar, may be used in accordance with the present disclosure.

The VNF layer 120 may additionally include a coordinator and data collector 122; the coordinator and data collector 122 may also be referred to as a data collector and coordinator of mapper functions 122. The data collector and coordinator of mapper functions 122 may be a solitary component, may be a combination of a discrete data collector and a discrete coordinator of mapper functions, may be a collection of subcomponents that perform the functions of the data collector and coordinator of mapper functions 122, or some combination thereof.

The coordinator and data collector 122 may include a movement tracker 122a, a user movement manager 122b, a map segmentation engine 122c, a user trajectory locator 122d, a data collector demon 122e, a map-based classifier 122f, a coordinate collector service 122g, metadata mapper classes 122h, one or more stream-based candidate classifiers 122i, a service interconnect application programming interface (API) 122j, and a vector derivator 122k. The coordinator and data collector 122 may communicate directly with the display 102, or a subcomponent of the coordinator and data collector 122 (such as the movement tracker 122a, as shown in FIG. 1) may communicate directly with the display 102, or the VNF layer 120 may communicate directly with the display 102 such that information is funneled up as necessary from a subcomponent (such as a movement tracker 122a) to a component (such as the coordinator and data collector 122) to the VNF layer 120 for transmission to and/or from the display 102.

Similar communications may be established between a service orchestration (such as for feedback and improvement) 106 and a service interconnect API 122j. The service orchestration 106 may be in direct communication with the service interconnect API 122j, with the coordinator and data collector 122, and/or with the virtual network function layer 120. Likewise, user and/or participant location data 104 (as shown in FIG. 1 by a user/participant location table 104) may communicate directly with the service interconnect API 122j, with the coordinator and data collector 122, and/or with the VNF layer 120. The display 102, service orchestration 106, and user/participant location data 104 may communicate with the VNF layer 120, its various components, and/or subcomponents as is necessary or desired as will be understood by those skilled in the art.

The VNF layer 120 may also include a map and coordinate structure (STRUCT) generator 124. The map and coordinate STRUCT generator 124 may include a map generator 124a, a situation of viability mapper subcomponent 124b, a tag generator 124c, and an object tagging subcomponent 124d. The VNF layer 120 may also include a channel management and orchestration connector 126.

The VNF layer 120 may be coupled with or communicably connected with a VNF communication interface 150, also referred to as a VNF interface 150. The VNF interface 150 may be in communication with one or more physical network functions 160, 162, 164, 166, and 168. A physical network function (PNF) 160 is shown in greater detail; the same subcomponents of PNF 160 may be used in any other PNF 162, 164, 166, and 168 in accordance with embodiments of the present disclosure.

A PNF 160 may include a variety of subcomponents such as a mobility manager 160a, a resource manager platform interface 160b, a VNF interconnect API 160c, and a bearer slicing 160d such as a radio bearer slicing 160d. A PNF 160 may include a universally unique identifier (UUID) mapper and/or an international mobile equipment identity (IMEI) mapper, shown together in FIG. 1 as a UUID and IMEI mapper 160e. A PNF 160 may include a channel monitor 160f, a dedicated traffic channel (DTCH) allocation map 160g, and a channel bandwidth allocation logic component 160h.

A channel monitor 160f may include information such as one or more DTCH identities (ID) and any affiliated UUIDs. Likewise, the DTCH allocation map 160g and/or channel bandwidth logic component 160h may include one or more DTCH IDs, their affiliated allocated bandwidths, and quality of service (QoS) class identifier (QCI) indices.

Each PNF 160, 162, 164, 166, and 168 may have a related IoT instance. FIG. 1 provides the examples of PNF 162 with an IoT instance embedded in a motorcycle helmet 172, PNF 164 with an IoT instance as part of a public safety vehicle such as an ambulance 174, and PNF 166 with an IoT instance of a vehicle 176 such as a personal, private, or commercial vehicle 176. Other IoT devices will be suitable for use in accordance with the present disclosure as will be understood by a person having ordinary skill in the art.

In some embodiments of the present disclosure, stream data for a device trajectory may be parsed and saved in mapper objects. In some embodiments, mapper objects may be supplied to a movement tracker 112, 122a, and/or 112b. A movement tracker 112, 122a, and/or 112b may be used in a network architecture instance (e.g., a VNF) or in a user instance (e.g., the IoT device of a user or participant). In some embodiments, mapper objects are provided to the movement tracker to trigger decisions regarding the location of a user endpoint (UE) or UE-set. In some embodiments, gyrometric information may be used to classify vector mappers for virtual elevations and altitude.

Figure 2:
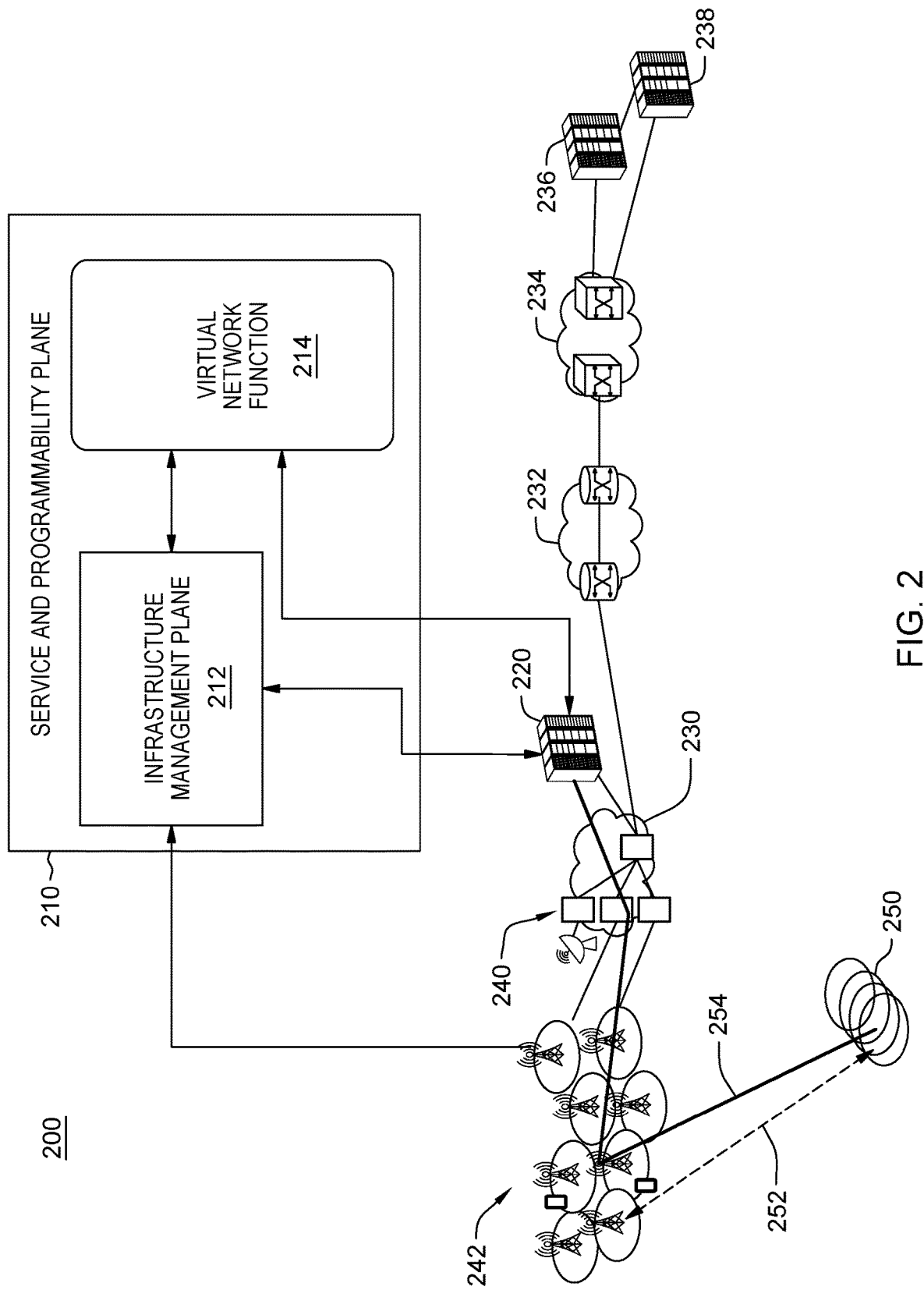
FIG. 2 depicts a system for tracking infection in accordance with some embodiments of the present disclosure.

FIG. 2 depicts a system 200 for tracking infection in accordance with some embodiments of the present disclosure. The system 200 includes a service and programmability plane 210 with an infrastructure management plane 212 and a VNF 214. The infrastructure management plane 212 and the VNF 214 may be in direct communication with each other, as shown in FIG. 2, or may funnel communications betwixt themselves through the service and programmability plane 210. The service and programmability plane 210 may be in communication with external components such as the cloud 220 and one or more radio devices 242. The infrastructure management plane 212 and VNF 214 may communicate directly with radio devices 242 and/or the cloud 220, or the infrastructure management plane 212 and VNF 214 may communicate with radio devices 242 and/or the cloud 220 via the service and programmability plane 210.

The radio devices 242 shown in FIG. 2 are radio towers 242 which communicate via radio waves. Radio devices 242 may be, for example, one or more radio transceivers 242. As the service and programmability plane 210, infrastructure management plane 212, and/or VNF 214 may accept various types of communications, other communicative technologies may be used in accordance with the present disclosure such as other electromagnetic communications, light transmittance, semaphore, sound, other vibrations, and datagrams.

Radio devices 242 may communicate with a device 250 via a control and data protocol data unit (PDU) 252. In some embodiments, the control and data PDU 252 will use 5G technology for communications between the radio devices 242 and the device 250.

The device 250 may be an IoT-enabled device, such as a smartphone, voice controller, doorbell camera, light switch, air quality monitor, thermostat, remote, vehicle or vehicle component, or a homemade device constructed with an IoT board. In some embodiments, the device 250 will be 5G enabled and will use 5G communication technologies when communicating with a radio device 242.

In some embodiments, the device 250 may communicate directly with the service and programmability plane 210. This direct communication may be established via, for example, a dedicated channel 254 connecting the device 250 to the cloud 220 via a fronthaul/backhaul network 240 and an optical access network 230. A direct communication may be established by way of, for example, a virtual private network (VPN) between the device 250 and the service and programmability plane 210 which may funnel communications through radio devices 242, a fronthaul/backhaul network 240, an optical access network 230, and the cloud 220 without granting the radio devices 242, fronthaul/backhaul network 240, optical access network 230, or cloud 220 access to the transmitted data. A similar communicative link may be established between the device 250 and the infrastructure management plane 212 and/or the device 250 and the VNF 214.

The cloud 220 may be an edged cloud 220 with one or more subsets of programs that run with a set of data values to enable faster, edged computation for users. Core clouds 236 and 238 are less likely to have these subsets of programs running because user experience is not likely to experience the same level of improvement from faster, edged computation.

Radio devices 242 may be connected to a fronthaul/backhaul network 240. The fronthaul/backhaul network 240 is one or more communication networking entities 240. The fronthaul/backhaul network 240 may be connected to the optical access network 230. The optical access network 230 may be connected to an optical metro network 232, an optical core network 234, and one or more core clouds 236 and 238.

In some embodiments, a dedicated channel 254 (such as a dedicated 5G channel) may connect a participant device 250 (such as an IoT device 250) to a cloud edge 220, service and programmability plane 210, infrastructure management plane 212, or VNF 214. A dedicated channel 254 may be used, for example, to prevent unauthorized access to personal, private, or otherwise confidential information. Similar, the same, different, or information additional to the information communicated from the participant device 250 to the cloud edge 220, service and programmability plane 210, infrastructure management plane 212, or VNF 214 may be communicated to local radio towers 242 via a PDU 252 such as a 5G control and data PDU 252.

Various components used in accordance with the present disclosure enable or increase privacy protection. For example, using a DTCH, UUID, IMEI, or dedicated channel 254 may permit privacy to be maintained while sharing personal data by preventing users from viewing private participant data. In some embodiments, a combination of DTCH, UUID, IMEI, and dedicated channels 254 may be used.

In some embodiments of the present disclosure, a network architecture (such as a VNF) may abstract the identity of a participant and/or of a participating device by use of logical channel identification to preserve privacy of the participant. By using logical channel IDs, services in an orchestration plane cannot be backtracked to obtain participant data such as international mobile subscriber identity (IMSI) and temporary mobile subscriber identity (TMSI) because identifiers may be abstracted in, by, or through the network architecture. This abstraction of data may preserve privacy of a participant by preventing unauthorized access to personal, sensitive, and/or confidential information.

In some embodiments of the present disclosure, the network architecture may support features protecting participant information between the user UE and the network architecture by way of a dedicated traffic channel-to-user endpoint (DTCH-to-UE) translation at the network architecture. In some embodiments, the DTCH may be used for logical slicing of a physical bearer to pinpoint information which may articulate insights helpful in making travel decisions (such as informing a participant of ticketing permissions and/or restrictions) while preserving the privacy of the participant.

In some embodiments of the disclosure, a VNF of a 5G telecom network may be used to generate and update a dynamic infection map. In some embodiments of the disclosure, a component may collect data from one or more IoT devices situated on or within a vehicle via logical connection identities and thereby initiates stream-based data collection requests. The present disclosure further provides that location information may be among the data requested, such as relative location or latitudinal and longitudinal coordinates.

In some embodiments of the present disclosure, location information of sites or objects of potential infection may be saved in metadata mapper classes. This information may be used to compare locations of various objects, such as to compare the location of a potentially infected IoT device with the location of another object to determine whether a close proximity may have resulted in the other object being infected by the potentially infected IoT device. In some embodiments, a participant and/or user may be determined to be in the proximity of, or to not be in proximity of, a potentially infected object by cross-verifying the participant and/or user location with the location of the object.

In some embodiments of the present disclosure, a 5G-DTCH datastream may be initiated to a participating IoT device to instruct the 5G-DTCH device to submit information to a network architecture. Information requested from the IoT device may include the location of the participating IoT device, the materials that make up the IoT device (e.g., plastic, stainless steel, and/or ceramics), and environmental as well as other situational data. The information requested may be in the form of a multi-level DTCH list of UUID information which may articulate situational insights to update an infection map. A DTCH list, in accordance with the present disclosure, may be a list of 5G logical channels between an IoT device and a femtocell or small cell (e.g., an eNodeB). The femtocell or small cell may be extended to a VNF via a bearer (such as an S1 bearer of a 5G network). Logical channels generated by UE devices may send and/or receive information over a radio bearer (such as an NR), and the VNF may track a DTCH connected to a device.

In some embodiments of the present disclosure, a VNF may perform segmented location with the location information of an IoT device: a total area may be segmented into a number of subregions to reduce the complexity of the location matching algorithm, and the location of the IoT device and the location of the participant may be matched. If the locations of an IoT device and a participant are matched, a vector-based trajectory may be generated; this vector-based trajectory may, for example, determine whether a participant is in a vehicle and traveling, in a stationary vehicle (such as a parked vehicle), stationary and not in a vehicle, or traveling outside of a vehicle.

In some embodiments of the present disclosure, a participating IoD device may be a vehicle component. If a participant is in a moving vehicle, the network architecture (such as a VNF) may monitor the trajectory of the vehicle via the IoT device. Observing a vehicle stop event (such as through indication by vector symbols), may trigger the network architecture may request environmental data from the IoT device. Environmental information the network architecture may request may include ambient temperature, humidity, location, gyrometric trajectory vectors, sunlight intensity status, and other information which may impact viability of a pathogen.

In some embodiments of the present disclosure, a participating IoD device may be a vehicle component, and a vector-based trajectory may be used to identify whether a participant is in the vehicle with the participating vehicle component. In some embodiments, the network architecture may monitor a trajectory, such as a destination trajectory, while the vehicle is mobile. In some embodiments, the network architecture may identify a stop event (e.g., the vehicle is parked), and the network architecture may request the vehicle collect environmental data at the stop location and submit it to the network architecture.

In some embodiments of the present disclosure, information may be structured and submitted to a network architecture (such as a VNF instance). The network architecture may calculate pathogen viability and the length of time a pathogen may be viable based on information collected from an IoT device and database information. Weightage-based filtering may be used to calculate the lifespan of the pathogen. Viability and expected viability time may be displayed on a map for a user to view real time information about the infection in a region. The map of infection may be viewed by users in a variety of ways, such as via a website, a smartphone application, a multidomain orchestration plane, or other ways which will be recognized by those skilled in the art.

Figure 3:
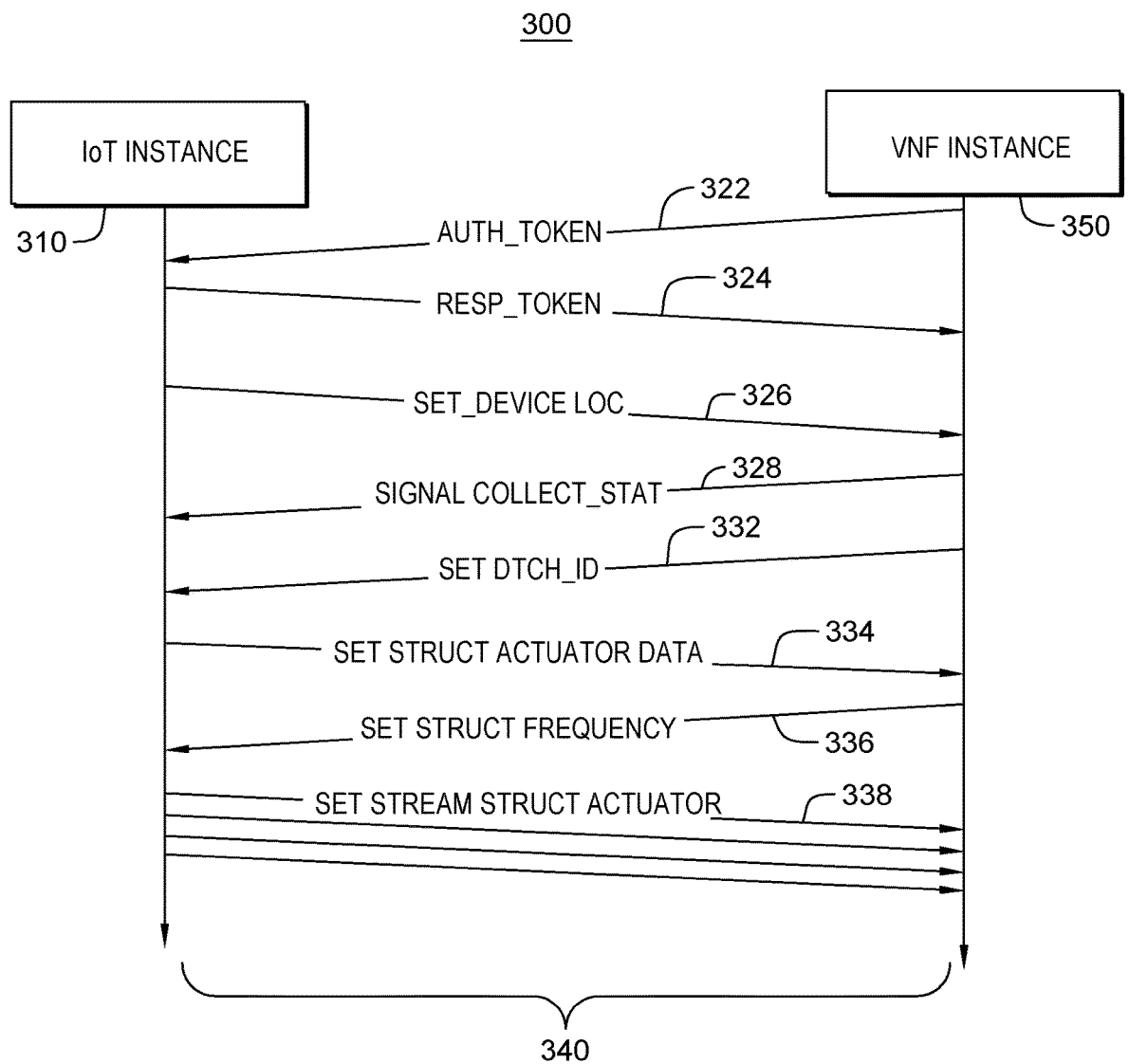
FIG. 3 illustrates an exchange of information between a user instance and a service provider instance in accordance with some embodiments of the present disclosure.

FIG. 3 illustrates an exchange of information 300 between a user instance 310 and a service provider instance 350 in accordance with some embodiments of the present disclosure. The user instance 310 may be an IoT instance 310. The service provider instance 350 may be a VNF instance 350 such as a VNF instance for an infection map service 350. Information exchanged 340 may be instantaneous, near instantaneous, or occur over time; in FIG. 3, the exchange is depicted as occurring nearly instantaneously as indicated by the slight slant of the lines of communication 340 (whereas an instantaneous communication could instead be depicted by using horizontal lines).

The information exchanged 340 may include the service provider instance 350 sending the user instance 310 an authorization component 322 such as an authorization token 322. The user instance 310 may then respond with a response token 324 and device location data 326. The service provider instance 350 may transmit a signal to collect statistical information 328 either to retrieve information not yet received by the service provider instance 350 or to verify information that the service provider instance 350 has received. The service provider instance 350 may set a DTCH_ID 332 for the user instance 310. The user instance 310 and service provider instance 350 may exchange settings for structure actuator data 334 and structure frequency 336. The user instance 310 and service provider instance 350 may set a stream structure actuator 338 to activate sensors and commence an exchange of data. Once the stream structure actuator is set 338, the data exchange may be comparably open; in other words, once the user instance 310 and the service provider instance 350 have established communication protocols, relevant data may pass between the user instance 310 and the service provider instance 350.

Information exchanged 340 between the user instance 310 and the service provider instance 350 may be shown in one direction, but a person having ordinary skill in the art will recognize that any information may travel in either direction. For example, the system 300 depicts the service provider instance 350 initiating communication by submitting an authorization token 322 to a user instance 310. However, the user instance 310 may instead initiate communications by submitting the authorization token 322 to the service provider instance 350; in such a case, the service provider instance 350 would respond with a response token 324.

In some embodiments of the present disclosure, a service provider instance 350 may notify the user instance 310 of one or more local instances of infection. A notification of infection may be used for various purposes such as: to enable a user to avoid the instance of infection; to notify a disinfection or fumigation team of a site or object that may require fumigation; and/or for logistical management of fumigation such as to enable efficient scheduling of fumigation supported by pathogen viability timeline data. For example, a user may be a parking enforcement agent, and the parking enforcement agent may be prompted to stay away from a vehicle that has been identified as infected, or the parking enforcement agent may be prompted to set a warning sign near an infected vehicle to direct pedestrians away from the vehicle.

In some embodiments of the present disclosure, an end-to-end (E2E) multi-domain service orchestration layer may be used. In some embodiments, a communication handshake may be established to assist with the facilitation of information transference and infection monitoring services within the programmability framework. In some embodiments, a server or service authentication may be used in the present disclosure using an authorization protocol such as a 5G interservice authorization protocol. In some embodiments, coordinated region mappers may be used to collect streams of data and save the datastreams into metadata mapper objects.

In some embodiments of the present disclosure, movement of infected participants may be tracked, and the derived coordinates of infected participants may be mapped with IoT object locations. In some embodiments, location information (such as latitude and longitude coordinates) may be used to verify that a participant is in the same location as an IoT object. In some embodiments, the trajectory of a person and an object may lead to the conclusion that the person is traveling in a vehicle.

In some embodiments of the present disclosure, object-situated actuators may be triggered to collect environmental details and submit these environmental details to the network architecture. Environmental details may include, for example, ambient temperature, humidity, location, and whether the object is in direct sunlight. In some embodiments, the network architecture may request additional information from the object, such as peripheral atmospheric information; peripheral atmospheric information may include any environmental details not previously submitted, including information to verify information that was previously submitted. In some embodiments, data structures may be submitted to the network architecture and polling demon to capture stream-based information.

In some embodiments of the present disclosure, the generation of an infection map may be derived from atmospheric evidence. In some embodiments, collected information and insights may be used to identify a pathogen and the infection viability of the pathogen. In some embodiments, weightage-driven filtering of information may be used to generate an infection or pathogen viability map based on object information. In some embodiments, the object is a vehicle, and relevant information about the vehicle may include the materials that comprise, and/or the coating of the materials, of the various components of the vehicle.

In some embodiments of the present disclosure, a participant may opt to share information via one or more sensors of an IoT device. For example, a vehicle (e.g., user instance 310) may have built in humidity, temperature, location identification (such as global positioning service (GPS) equipment), camera/visual, and microphone/audio sensors, and a participant may decide to share information collected by the vehicle with a service provider instance 350 such as a network architecture instance 350. In some embodiments, the participant may decide to automatically share information collected by the vehicle with the network architecture.

In some embodiments of the present disclosure, a network architecture instance may request a user instance 310 collect information such as ambient temperature, humidity, parking status, motion, velocity, location, gyrometric trajectory vector, camera/visual, light intensity, and other information and submit the information to the network architecture instance. In some embodiments, data streamed between a network architecture instance and a user instance 310 may be classified using serial or parallel stream-based classifiers. In some embodiments, classification of streamed data may articulate situational insights. In some embodiments, situational insight may be conveyed to a user instance 310 via, for example, a display on the user instance 310 which may overlay a map such as a vector or infection map.

In some embodiments of the present disclosure, one or more static computing programs may be invoked to collect location service trajectory maps, device location functions, map segmentation mapping, and related information. In some embodiments, data structure information may be extracted to a service database such as a network architecture instance 350.

In some embodiments of the present disclosure, a network architecture instance 350 may receive an initial or new structure or structure protocol for a user instance 310. The network architecture instance 350 may update filtering mechanisms based on the initial or new structure or structure protocol. In some embodiments, a structure may be shared for information concerning virus viability functions using an existing mapping database and experimental analysis. In some embodiments, the viable time period of a pathogen and weightage-based filtering may be applied on information (such as temperature, humidity, and location) collected from one or more user instances 310 to calculate the lifespan of the pathogen.

In some embodiments, information sent from a network architecture instance 350 to a user instance 310 may include map-based classifier information to generate or update a real time map of infection. In some embodiments, tags may be selected from settings or configuration files that include or exclude specified information (such as pathogen viability, probable viability period, likelihood of infection at various distances from an infection epicenter, and other data). In some embodiments, a data structure map may be generated and updated with a filtering for API-driven consumption enablement.

Figure 4:
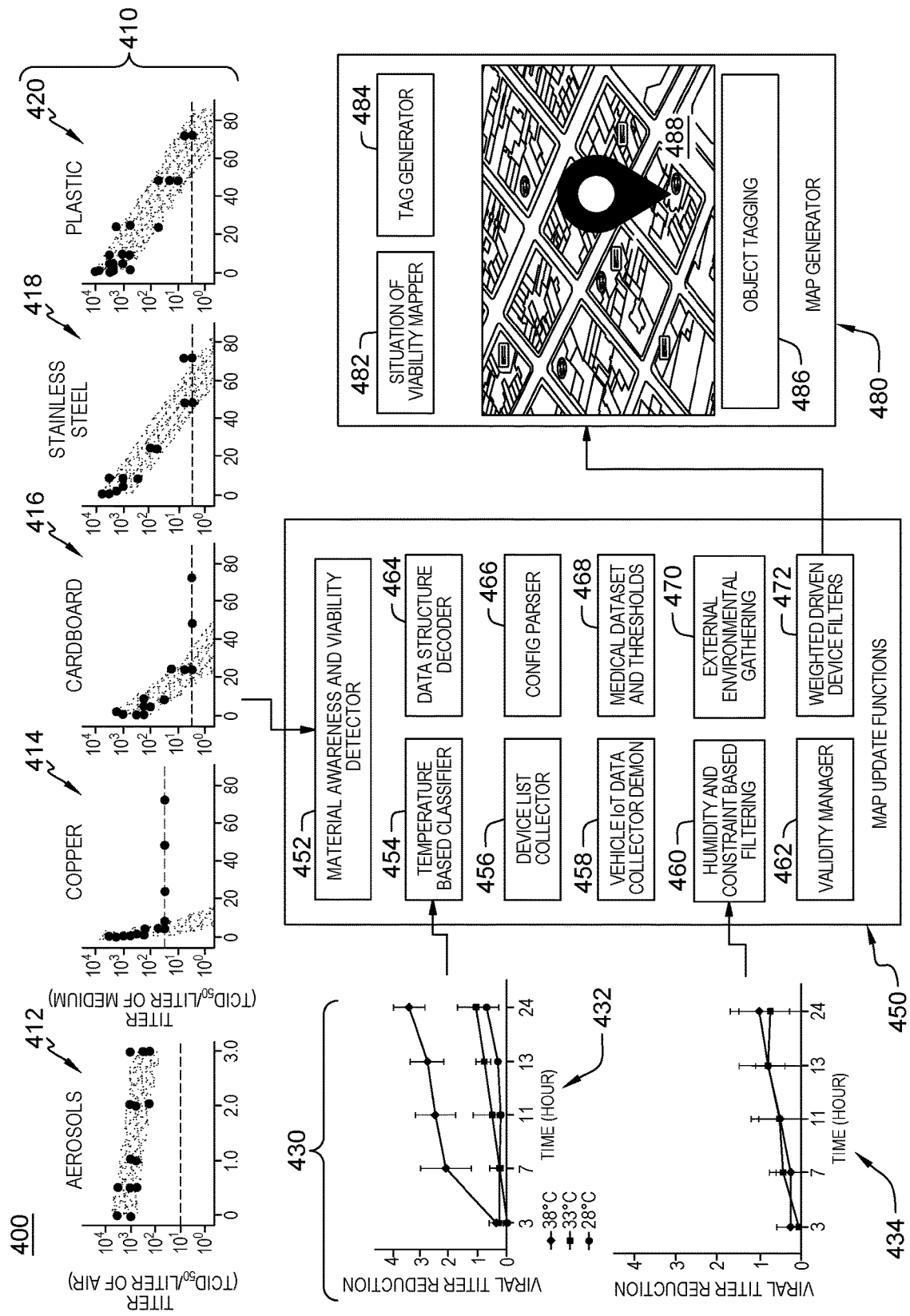
FIG. 4 depicts a system for tracking infection a in accordance with some embodiments of the present disclosure.

FIG. 4 depicts a system 400 for tracking infection and displaying information to a user in accordance with some embodiments of the present disclosure. Information 410 and 430 is submitted to a processor 450 which uses the information 410 and 430 to compute data which may then be displayed on a display device 480.

Information 410 and 430 may include viability data of a pathogen dependent on a surface the pathogen is in contact with 410. Surface-dependent viability data 410 is depicted in FIG. 4 as graphs 412, 414, 416, 418, and 420 with concentration depicted over time. Concentration is displayed on y-axes in titers; the graph conveying information for aerosols 412 uses $TCID_{50}$ per liter of air units for titers and the graphs conveying information about the solid surfaces of copper 414, cardboard 416, stainless steel 418, and plastic 420 uses $TCID_{50}$ per milliliter of the relevant medium units for titers. Other viability data 410 may also be submitted to the processor 450 such as, for example, the viability of different pathogens, or the viability of the same pathogen on different surfaces. Viability data 410 may be submitted in other forms; for example, spreadsheets, databases, or data trends may be used.

Information 410 and 430 may include viability data of a pathogen dependent on environmental conditions 430. Environmental conditions data 430 may include temperature data 432 and humidity data 434. Environmental-dependent viability data 430 is depicted as viral titer reduction over time for various temperatures while other environmental constraints (e.g., humidity) are held constant. Viral titer reduction is displayed on the y-axes and time is displayed on the x-axes. The temperatures used for the example temperature dataset 432 displayed are 38° Celsius, 33° Celsius, and 28° Celsius; data on other temperatures and/or for other pathogens may also be useful.

Information 410 and 430 may be generally referred to as situational data. Situational data 410 may include any data derived from a situation that may impact the viability of a pathogen. For example, situational data 410 may include ambient temperature, humidity, sunlight exposure, cloud cover, wind conditions, pollution, material a pathogen has come into contact with, conditions of the material a pathogen has come into contact with, and other data about the circumstances.

Situational data 410 may include information about an object a pathogen has come into contact with, such as a vehicle, a table, a baseball, a telescope, an animal, or another surface that may retain a pathogen. Relevant information about the object may include the location of the object, the material of the object, the temperature of the material of the object, or other information that may impact pathogen viability.

Information 410 and 430 may be submitted to a processor 450 such as a device which can integrate data and update a map 450. The processor 450 may thus be a single unit 450 capable of performing various map update functions or it may be a collection of subunits 452, 454, 456, 458, 460, 462, 464, 466, 468, 470, and 472 each capable of contributing to a goal of updating information displayed to a user. If the processor 450 has subunit 452, 454, 456, 458, 460, 462, 464, 466, 468, 470, and 472, then information 410 and 430 may be submitted directly to the relevant subunit or submitted to the processor 450 which may submit the information 410 and 430 to the proper subunit.

The processor 450 may include a material awareness and viability detector 452, a temperature database 454 such as a temperature-based classifier 454, and a humidity database 460 such as a humidity and constraint-based filter 460. The processor 450 may include a device list collector 456, an IoT data collector demon 458, and a validity manager 462. The processor 450 may include a data structure decoder 464 and a configuration parser 466. The processor 450 may include one or more device filters 472 such as weighted device filters 472, driven device filters 472, or weighted driven device filters 472. The processor 450 may include a medical dataset 468 which may include thresholds and an external environmental information gathering component 470 which may gather various types of data from the environment. The external environmental information gathering component 470 may collect data directly, such as a thermometer taking ambient temperature, or it may collect data indirectly, such as by connecting to the internet, submitting the processor 450 location to a weather database, and receiving the current forecast for the current location of the processor 450.

Viability data of a pathogen dependent on a surface the pathogen is in contact with 410 may be submitted to the processor 450 or directly to the material awareness and viability detector 452. Temperature viability data 432 may be submitted to a temperature-based classifier 454 subcomponent of a processor 450. Humidity viability data 434 may be submitted to a humidity and constraint-based filtering subcomponent of a processor 450. Viability data of a pathogen dependent on environmental conditions 430 may alternatively be submitted to an environmental data subcomponent (not shown) which accepts and takes into consideration both the temperature data 432 and the humidity data 434.

The processor 450 may process the various information concerning the viability of the relevant pathogen, material awareness information, participant information, and other information and submit the resulting data to a display device 480 such as a map generator 480. The display device 480 may then generate a map 488 to be displayed on a display 488 for a user. The generated map 480 may include the location of the user as well as indicate locations of possible infection and the likelihood of viability of the pathogen causing infection at each infected site. A user may opt against sharing location data such that the generated map 488 would not display the user location but the generated map 488 may still display possible infection sites and the likelihood of viability of the pathogen causing infection at each infected site.

The display device 480 may include options for a user. Such options may include a situation of viability mapper 482 option which may enable a user to input additional situational data (e.g., whether a vehicle a participant is using is perked in direct sunlight) into the system 400. The display device 480 may include a tag generator 484 to enable a user to manually input tags (e.g., place an infection marker in a location that shows signs of infection). The display device 480 may include an object tagging feature 486; such a feature may enable a participant to tag an object which the participant has interacted with to notify users that the object may be infected.

Participant information may include information about the infectiousness of a participant, the location of the participant, whether the participant is inside a vehicle (such as a car), or other relevant information. For example, the infectiousness of a participant may be information submitted by the participant from a recent diagnosis. Infectiousness of a participant may instead be a participant volunteering information about contact with a possibly infected individual (or lack of contact with anyone over a set amount of time), the submission of symptom information indicative of infectiousness, or other information which may indicate infectiousness. Infectiousness may be entered manually, such as a participant entering the information into the system 400, or it may be collected automatically, such as a participant permitting the system 400 to collect information and the system 400 collecting the information. Automatic information collection may be a one-time occurrence, such as a participant pressing a button to permit the system 400 to collect information at one period in time, or it may occur over multiple instances, such as a participant granting permission for the system 400 to collect information periodically.

Periodic information collection may occur every set period of time (e.g., once per day) or upon a specified collection trigger (e.g., pressing a button). Periodic information collection may also include continuous or constant information collection (e.g., updating the location of the participant as the participant drives across a region). Certain information may be continuously or constantly monitored such that a certain condition that is monitored may trigger the automatic collection of data; the system 400 may monitor a participant for one or more symptoms and collect information accordingly.

Automatic and manual information collection may occur in concert. For example, a participant may manually enter that the participant visited a relative in the hospital with a certain contagion; the participant may then permit the system 400 to monitor conditions and symptoms such that if the participant either develops a symptom (such as a cough) or fails to develop any symptoms, then the processor 450 pulls the participant information, updates the likelihood of infection, and updates the device display 480 as the situation changes. In some embodiments of the present disclosure, a participant may opt for infection status to be displayed only to certain users (e.g., display only on the device of the participant or the device of the participant as well as the device of a friend identified via UUID or IMEI).

Other information may also be collected by the processor 450. For example, if a participant decides to tag an object 486 through the device display 480, the processor 450 may request additional information about the object. For example, the processor 450 may request what materials the object is made out of (e.g., whether a table is wooden or plastic), or the processor 450 may request identifying information about the object (e.g., make, model, and year of a car or the SKU of an off-the-shelf product) such that the processor 450 is enabled to look up the information online, update its calculations, and display infection data based on the most relevant information.

Figure 5:
FIG. 5 illustrates infection information displayed in accordance with some embodiments of the present disclosure.

FIG. 5 illustrates infection information displayed 500 in accordance with some embodiments of the present disclosure. Infection information may be displayed on a map 500. The dots on the map 500 represent sites of potential infection. The dots on the map 500 vary in size based on the likely viability of the infection at each site of potential infection. In FIG. 5, the larger a dot on the map 500 is, the more viable that instance of infection is. For example, the site of a known infection with high viability has a larger dot than a dot indicating the site of a potential but unconfirmed infection or the dot indicating a site of a confirmed infection where time has lapsed to the point of the contagion being less viable. A user may be able to obtain the location of an infected object, the probability of viability of the infection pathogen based on its viability data, and the general status of infection in the map area, among other information which may be helpful to imbed in the map.

Figure 6:
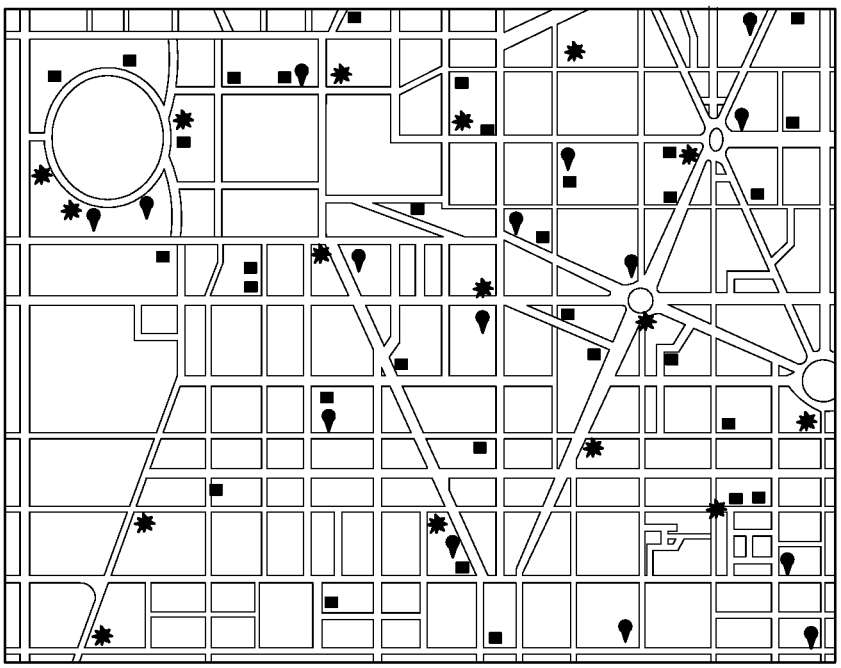
FIG. 6 illustrates infection information displayed in accordance with some embodiments of the present disclosure.

FIG. 6 illustrates infection information displayed 600 in accordance with some embodiments of the present disclosure. Infection information may be displayed on a map 600. The indicators on the map 600 represent sites of potential infection. The key in the corner of the map 600 indicates what each indicator means. In this map 600, an instance of high infection viability is shown as an exclamatory bubble with many points, an instance of moderate infection viability is shown as a circle with a solitary pointer, and an instance of low viability is shown with a square marker. Various indicators, colors of indicators, or other indicator attributes may be used to identify different levels of viability. Indicators may also be used to identify likelihood of infection or other factors. A user may be able to obtain the location of an infected object, the probability of viability of the infection pathogen based on its viability data, and the general status of infection in the map area, among other information which may be helpful to imbed in the map.

FIG. 5 and FIG. 6 illustrate two ways an infection map may be displayed to a user. Various symbols may be embedded in an infection map as will be understood by one skilled in the art. The map may include, for example, varying symbols for identifying the viability and probable viable time based on information collected from an IoT device. The infection map may be a data structure map generated from the relevant data. The infection map may be used by, for example, individual users, corporate users, governmental users, or other user groups.

In some embodiments of the present disclosure, maps may use color codes and symbols to indicate the viability of a pathogen. Color codes and symbols may be universal or may vary based on region. One reason color codes and symbols may vary based on region, for example, is that regional understanding of certain indicators may vary.

In some embodiments of the present disclosure, an API may be used to build intelligence within an instance or application of the present disclosure. In some embodiments, the API may enable coordination of data structures by using the infection map.

Figure 7:
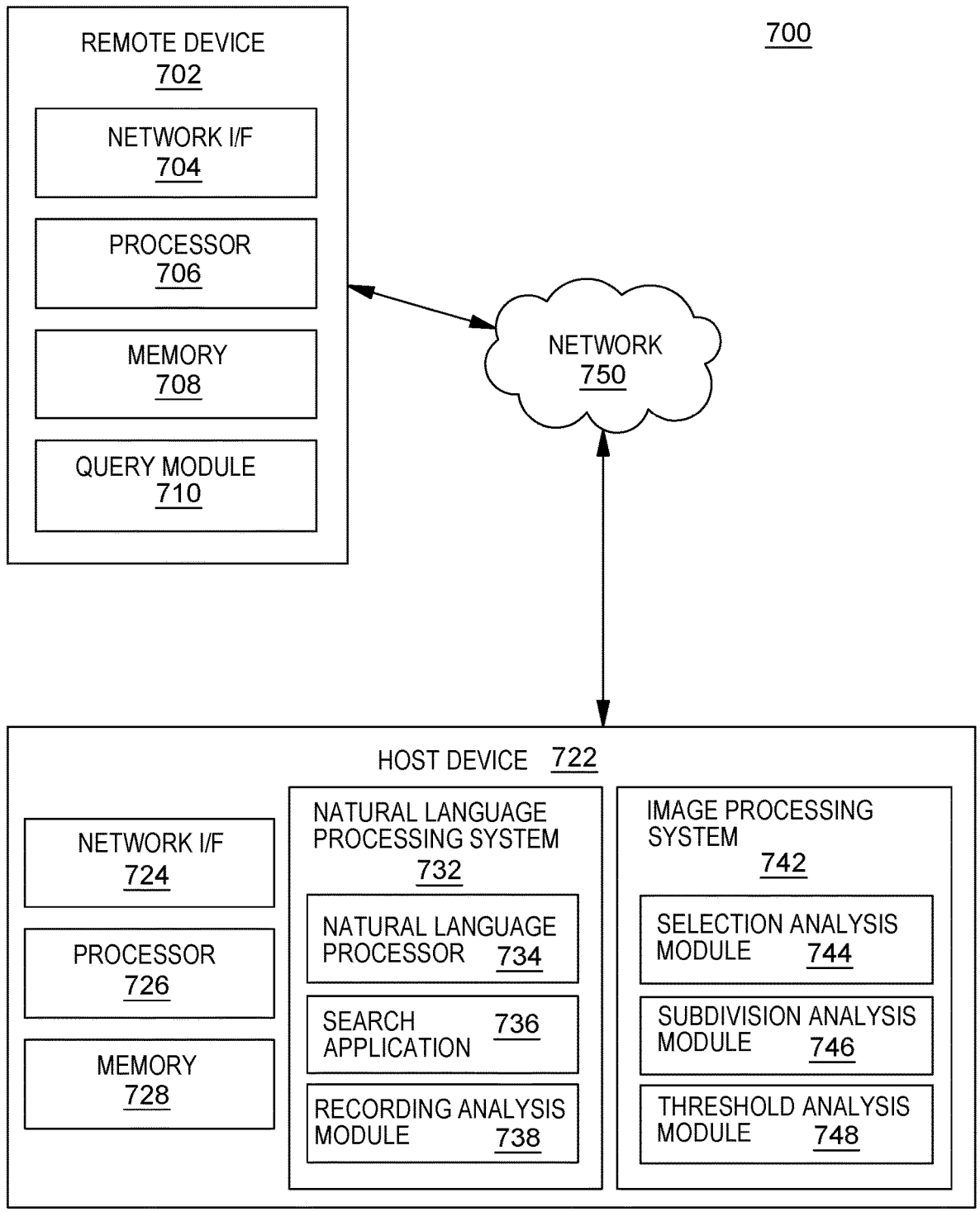
FIG. 7 depicts a block diagram of an example computing environment in which illustrative embodiments of the present disclosure may be implemented.

Some embodiments of the present disclosure may utilize a natural language parsing and/or subparsing component. Thus, aspects of the disclosure may relate to natural language processing. Accordingly, an understanding of the embodiments of the present invention may be aided by describing embodiments of natural language processing systems and the environments in which these systems may operate. Turning now to FIG. 7, illustrated is a block diagram of an example computing environment 700 in which illustrative embodiments of the present disclosure may be implemented. In some embodiments, the computing environment 700 may include a remote device 702 and a host device 722.

Consistent with various embodiments of the present disclosure, the host device 722 and the remote device 702 may be computer systems. The remote device 702 and the host device 722 may include one or more processors 706 and 726 and one or more memories 708 and 728, respectively. The remote device 702 and the host device 722 may be configured to communicate with each other through an internal or external network interface 704 and 724. The network interfaces 704 and 724 may be modems or network interface cards. The remote device 702 and/or the host device 722 may be equipped with a display such as a monitor. Additionally, the remote device 702 and/or the host device 722 may include optional input devices (e.g., a keyboard, mouse, scanner, or other input device) and/or any commercially available or custom software (e.g., browser software, communications software, server software, natural language processing software, search engine and/or web crawling software, filter modules for filtering content based upon predefined parameters, etc.). In some embodiments, the remote device 702 and/or the host device 722 may be servers, desktops, laptops, or hand-held devices.

The remote device 702 and the host device 722 may be distant from each other and communicate over a network 750. In some embodiments, the host device 722 may be a central hub from which remote device 702 can establish a communication connection, such as in a client-server networking model. Alternatively, the host device 722 and remote device 702 may be configured in any other suitable networking relationship (e.g., in a peer-to-peer configuration or using any other network topology).

In some embodiments, the network 750 can be implemented using any number of any suitable communications media. For example, the network 750 may be a wide area network (WAN), a local area network (LAN), an internet, or an intranet. In certain embodiments, the remote device 702 and the host device 722 may be local to each other and communicate via any appropriate local communication medium. For example, the remote device 702 and the host device 722 may communicate using a local area network (LAN), one or more hardwire connections, a wireless link or router, or an intranet. In some embodiments, the remote device 702 and the host device 722 may be communicatively coupled using a combination of one or more networks and/or one or more local connections. For example, the remote device 702 may be hardwired to the host device 722 (e.g., connected with an Ethernet cable) or the remote device 702 may communicate with the host device using the network 750 (e.g., over the Internet).

In some embodiments, the network 750 can be implemented within a cloud computing environment or using one or more cloud computing services. Consistent with various embodiments, a cloud computing environment may include a network-based, distributed data processing system that provides one or more cloud computing services. Further, a cloud computing environment may include many computers (e.g., hundreds or thousands of computers or more) disposed within one or more data centers and configured to share resources over the network 750.

In some embodiments, the remote device 702 may enable a user to input (or may input automatically with or without a user) a query (e.g., is any part of a recording artificial, etc.) to the host device 722 in order to identify subdivisions of a recording that include a particular subject. For example, the remote device 702 may include a query module 710 and a user interface (UI). The query module 710 may be in the form of a web browser or any other suitable software module, and the UI may be any type of interface (e.g., command line prompts, menu screens, graphical user interfaces). The UI may allow a user to interact with the remote device 702 to input, using the query module 710, a query to the host device 722, which may receive the query.

In some embodiments, the host device 722 may include a natural language processing system 732. The natural language processing system 732 may include a natural language processor 734, a search application 736, and a recording module 738. The natural language processor 734 may include numerous subcomponents, such as a tokenizer, a part-of-speech (POS) tagger, a semantic relationship identifier, and a syntactic relationship identifier.

The search application 736 may be implemented using a conventional or other search engine and may be distributed across multiple computer systems. The search application 736 may be configured to search one or more databases (e.g., repositories) or other computer systems for content that is related to a query submitted by the remote device 702. For example, the search application 736 may be configured to search dictionaries, papers, and/or archived reports to help identify a particular subject related to a query provided for a class. The recording analysis module 738 may be configured to analyze a recording to identify a particular subject (e.g., of the query). The recording analysis module 738 may include one or more modules or units, and may utilize the search application 736, to perform its functions (e.g., to identify a particular subject in a recording).

In some embodiments, the host device 722 may include an image processing system 742. The image processing system 742 may be configured to analyze images associated with a recording to create an image analysis. The image processing system 742 may utilize one or more models, modules, or units to perform its functions (e.g., to analyze the images associated with the recording and generate an image analysis). For example, the image processing system 742 may include one or more image processing models that are configured to identify specific images related to a recording. The image processing models may include a section analysis module 744 to analyze single images associated with the recording and to identify the location of one or more features of the single images. As another example, the image processing system 742 may include a subdivision module 746 to group multiple images together identified to have a common feature of the one or more features. In some embodiments, image processing modules may be implemented as software modules. For example, the image processing system 742 may include a section analysis module and a subdivision analysis module. In some embodiments, a single software module may be configured to analyze the image(s) using image processing models.

In some embodiments, the image processing system 742 may include a threshold analysis module 748. The threshold analysis module 748 may be configured to compare the instances of a particular subject identified in a subdivision of sections of the recording against a threshold number of instances. The threshold analysis module 748 may then determine if the subdivision should be displayed to a user.

In some embodiments, the host device may have an optical character recognition (OCR) module. The OCR module may be configured to receive a recording sent from the remote device 702 and perform optical character recognition (or a related process) on the recording to convert it into machine-encoded text so that the natural language processing system 732 may perform NLP on the report. For example, a remote device 702 may transmit a video of a medical procedure to the host device 722. The OCR module may convert the video into machine-encoded text and then the converted video may be sent to the natural language processing system 732 for analysis. In some embodiments, the OCR module may be a subcomponent of the natural language processing system 732. In other embodiments, the OCR module may be a standalone module within the host device 722. In still other embodiments, the OCR module may be located on the remote device 702 and may perform OCR on the recording before the recording is sent to the host device 722.

While FIG. 7 illustrates a computing environment 700 with a single host device 722 and a remote device 702, suitable computing environments for implementing embodiments of this disclosure may include any number of remote devices and host devices. The various models, modules, systems, and components illustrated in FIG. 7 may exist, if at all, across a plurality of host devices and remote devices. For example, some embodiments may include two host devices. The two host devices may be communicatively coupled using any suitable communications connection (e.g., using a WAN, a LAN, a wired connection, an intranet, or the Internet). The first host device may include a natural language processing system configured to receive and analyze a video, and the second host device may include an image processing system configured to receive and analyze .GIFS to generate an image analysis.

It is noted that FIG. 7 is intended to depict the representative major components of an exemplary computing environment 700. In some embodiments, however, individual components may have greater or lesser complexity than as represented in FIG. 7, components other than or in addition to those shown in FIG. 7 may be present, and the number, type, and configuration of such components may vary.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model with different physical and virtual resources dynamically assigned and reassigned according to demand. There is a sense of portion independence in that the consumer generally has no control or knowledge over the exact portion of the provided resources but may be able to specify portion at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but the consumer has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software which may include operating systems and applications. The consumer does not manage or control the underlying cloud infrastructure but has control over operating systems, storage, and deployed applications, and the consumer possibly has limited control of select networking components (e.g., host firewalls).

Deployment models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and/or compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
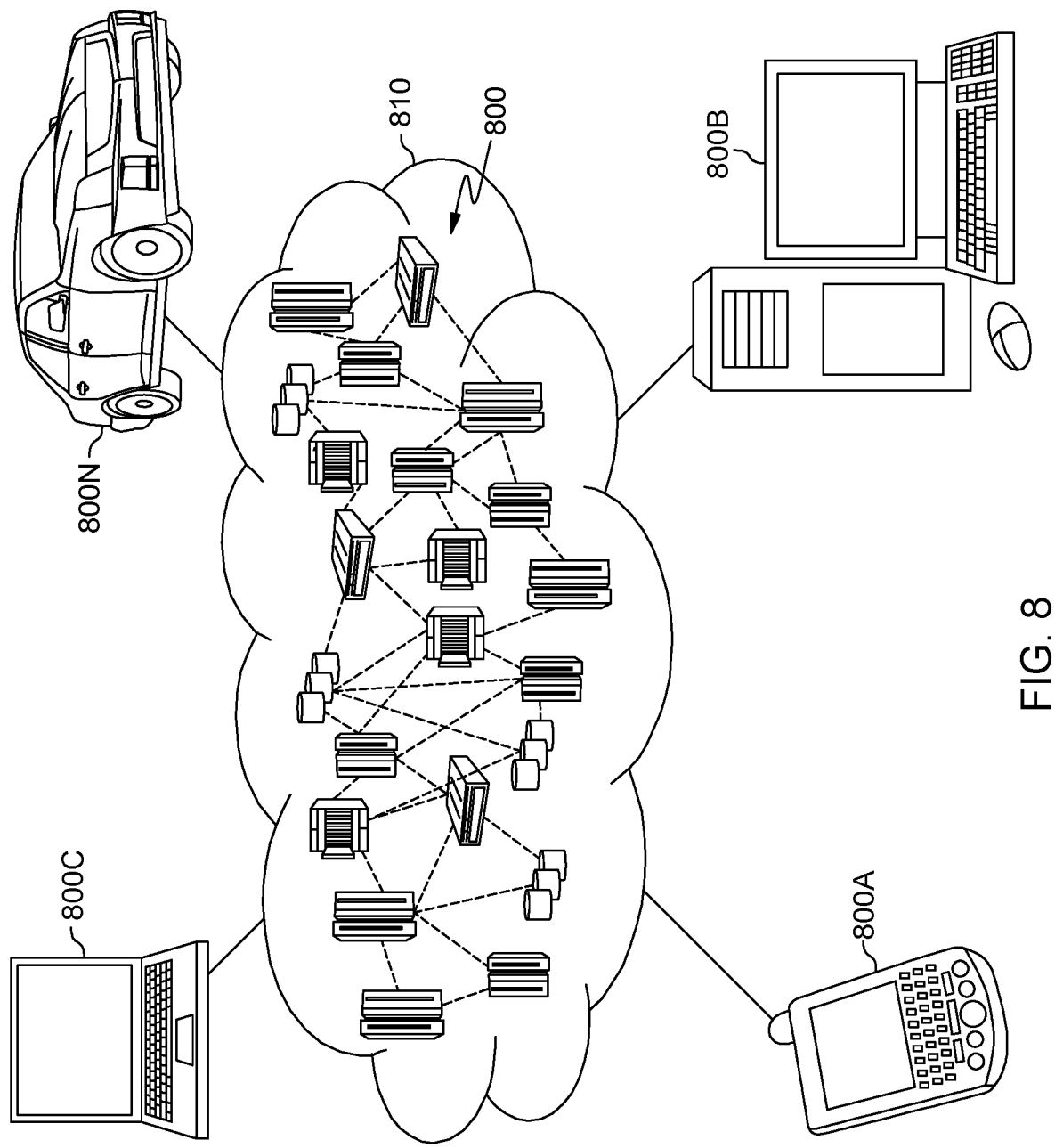
FIG. 8 illustrates a cloud computing environment in accordance with embodiments of the present disclosure.

FIG. 8 illustrates a cloud computing environment 810 in accordance with embodiments of the present disclosure. As shown, cloud computing environment 810 includes one or more cloud computing nodes 800 with which local computing devices used by cloud consumers such as, for example, personal digital assistant (PDA) or cellular telephone 800A, desktop computer 800B, laptop computer 800C, and/or automobile computer system 800N may communicate. Nodes 800 may communicate with one another. They may be grouped (not shown) physically or virtually, in one or more networks, such as private, community, public, or hybrid clouds as described hereinabove, or a combination thereof.

This allows cloud computing environment 810 to offer infrastructure, platforms, and/or software as services for which a cloud consumer does not need to maintain resources on a local computing device. It is understood that the types of computing devices 800A-N shown in FIG. 8 are intended to be illustrative only and that computing nodes 800 and cloud computing environment 810 can communicate with any type of computerized device over any type of network and/or network addressable connection (e.g., using a web browser).

Figure 9:
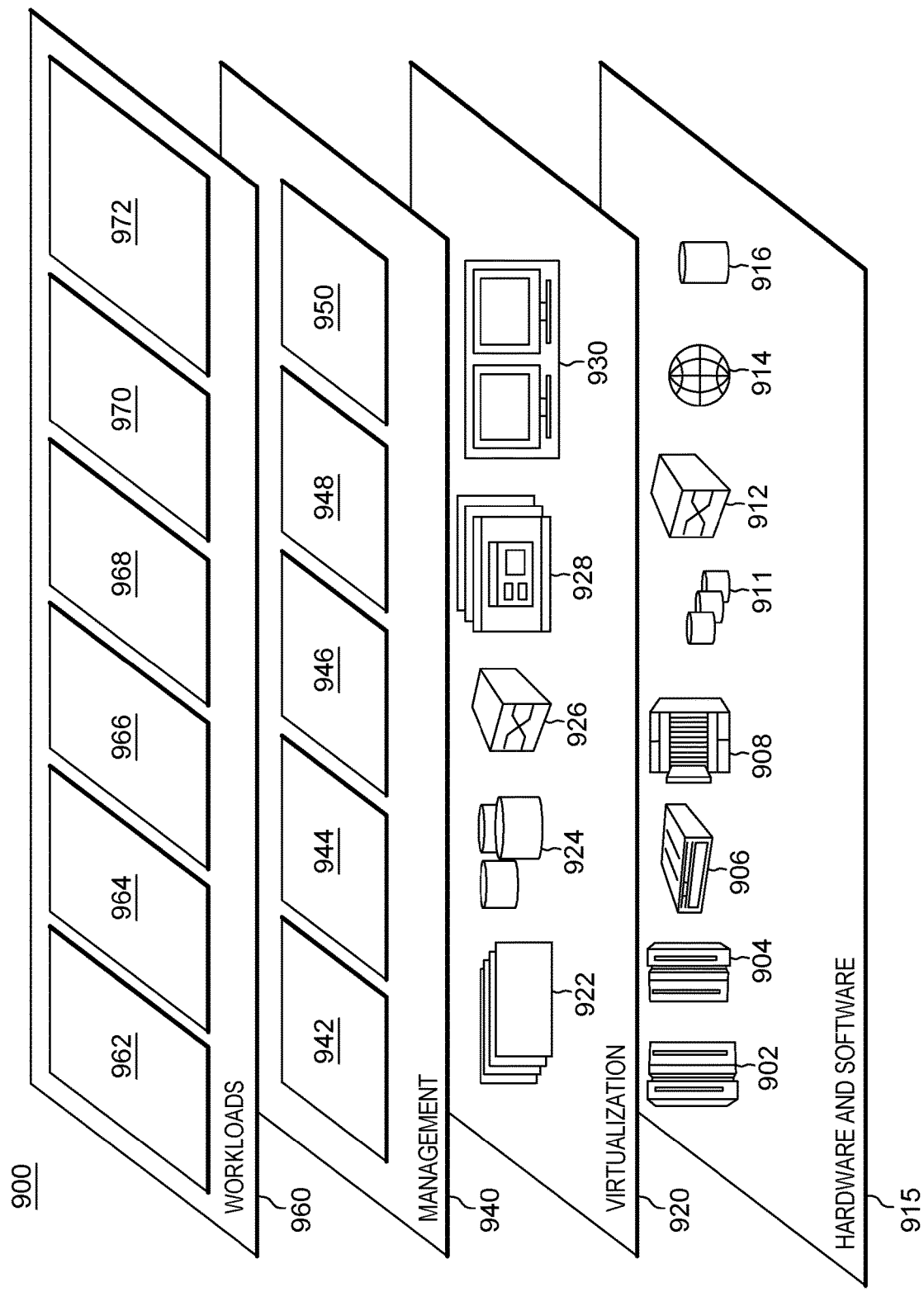
FIG. 9 depicts abstraction model layers in accordance with embodiments of the present disclosure.

FIG. 9 illustrates abstraction model layers 900 provided by cloud computing environment 810 (FIG. 8) in accordance with embodiments of the present disclosure. It should be understood in advance that the components, layers, and functions shown in FIG. 9 are intended to be illustrative only and embodiments of the disclosure are not limited thereto. As depicted below, the following layers and corresponding functions are provided.

Hardware and software layer 915 includes hardware and software components. Examples of hardware components include: mainframes 902; RISC (Reduced Instruction Set Computer) architecture-based servers 904; servers 906; blade servers 908; storage devices 911; and networks and networking components 912. In some embodiments, software components include network application server software 914 and database software 916.

Virtualization layer 920 provides an abstraction layer from which the following examples of virtual entities may be provided: virtual servers 922; virtual storage 924; virtual networks 926, including virtual private networks; virtual applications and operating systems 928; and virtual clients 930.

In one example, management layer 940 may provide the functions described below. Resource provisioning 942 provides dynamic procurement of computing resources and other resources that are utilized to perform tasks within the cloud computing environment. Metering and pricing 944 provide cost tracking as resources are utilized within the cloud computing environment as well as billing or invoicing for consumption of these resources. In one example, these resources may include application software licenses. Security provides identity verification for cloud consumers and tasks as well as protection for data and other resources. User portal 946 provides access to the cloud computing environment for consumers and system administrators. Service level management 948 provides cloud computing resource allocation and management such that required service levels are met. Service level agreement (SLA) planning and fulfillment 950 provide pre-arrangement for, and procurement of, cloud computing resources for which a future requirement is anticipated in accordance with an SLA.

Workloads layer 960 provides examples of functionality for which the cloud computing environment may be utilized. Examples of workloads and functions which may be provided from this layer include: mapping and navigation 962; software development and lifecycle management 964; virtual classroom education delivery 966; data analytics processing 968; transaction processing 970; and a tool for dynamically mapping infection 972.

Figure 10:
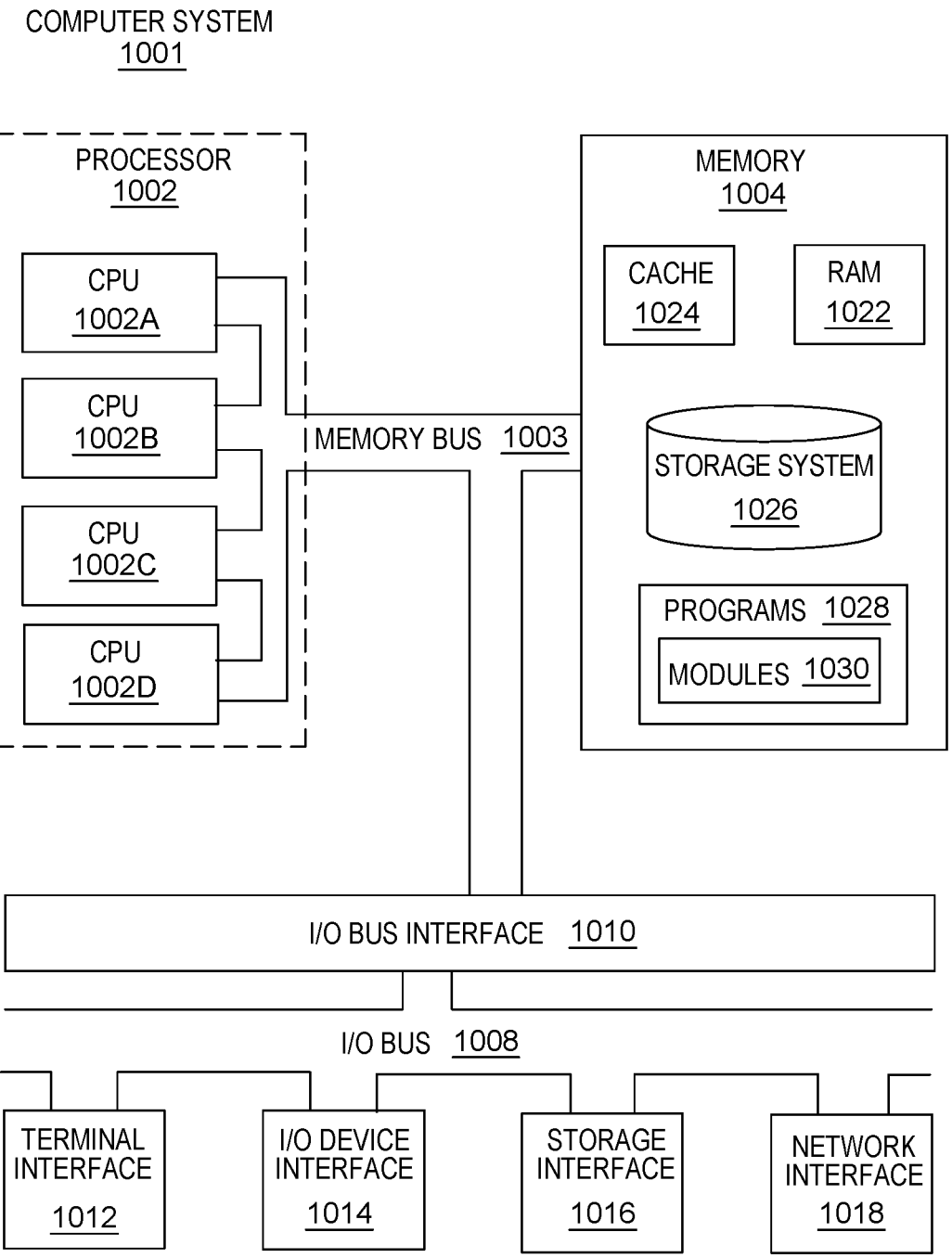
FIG. 10 illustrates a high-level block diagram of an example computer system that may be used in implementing one or more of the methods, tools, and modules, and any related functions, described herein, in accordance with embodiments of the present disclosure.

FIG. 10 illustrates a high-level block diagram of an example computer system 1001 that may be used in implementing one or more of the methods, tools, and modules, and any related functions, described herein (e.g., using one or more processor circuits or computer processors of the computer) in accordance with embodiments of the present disclosure. In some embodiments, the major components of the computer system 1001 may comprise a processor 1002 with one or more central processing units (CPUs) 1002A, 1002B, 1002C, and 1002D, a memory subsystem 1004, a terminal interface 1012, a storage interface 1016, an I/O (Input/Output) device interface 1014, and a network interface 1018, all of which may be communicatively coupled, directly or indirectly, for inter-component communication via a memory bus 1003, an I/O bus 1008, and an I/O bus interface unit 1010.

The computer system 1001 may contain one or more general-purpose programmable CPUs 1002A, 1002B, 1002C, and 1002D, herein generically referred to as the CPU 1002. In some embodiments, the computer system 1001 may contain multiple processors typical of a relatively large system; however, in other embodiments, the computer system 1001 may alternatively be a single CPU system. Each CPU 1002 may execute instructions stored in the memory subsystem 1004 and may include one or more levels of on-board cache.

System memory 1004 may include computer system readable media in the form of volatile memory, such as random access memory (RAM) 1022 or cache memory 1024. Computer system 1001 may further include other removable/non-removable, volatile/non-volatile computer system storage media. By way of example only, storage system 1026 can be provided for reading from and writing to a non-removable, non-volatile magnetic media, such as a "hard drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM, or other optical media can be provided. In addition, memory 1004 can include flash memory, e.g., a flash memory stick drive or a flash drive. Memory devices can be connected to memory bus 1003 by one or more data media interfaces. The memory 1004 may include at least one program product having a set (e.g., at least one) of program modules that are configured to carry out the functions of various embodiments.

One or more programs/utilities 1028, each having at least one set of program modules 830, may be stored in memory 1004. The programs/utilities 1028 may include a hypervisor (also referred to as a virtual machine monitor), one or more operating systems, one or more application programs, other program modules, and program data. Each of the operating systems, one or more application programs, other program modules, and program data, or some combination thereof, may include an implementation of a networking environment. Programs 1028 and/or program modules 1030 generally perform the functions or methodologies of various embodiments.

Although the memory bus 1003 is shown in FIG. 10 as a single bus structure providing a direct communication path among the CPUs 1002, the memory subsystem 1004, and the I/O bus interface 1010, the memory bus 1003 may, in some embodiments, include multiple different buses or communication paths, which may be arranged in any of various forms, such as point-to-point links in hierarchical, star, or web configurations, multiple hierarchical buses, parallel and redundant paths, or any other appropriate type of configuration. Furthermore, while the I/O bus interface 1010 and the I/O bus 1008 are shown as single respective units, the computer system 1001 may, in some embodiments, contain multiple I/O bus interface units 1010, multiple I/O buses 1008, or both. Further, while multiple I/O interface units 1010 are shown, which separate the I/O bus 1008 from various communications paths running to the various I/O devices, in other embodiments some or all of the I/O devices may be connected directly to one or more system I/O buses 1008.

In some embodiments, the computer system 1001 may be a multi-user mainframe computer system, a single-user system, a server computer, or similar device that has little or no direct user interface but receives requests from other computer systems (clients). Further, in some embodiments, the computer system 1001 may be implemented as a desktop computer, portable computer, laptop or notebook computer, tablet computer, pocket computer, telephone, smartphone, network switches or routers, or any other appropriate type of electronic device.

It is noted that FIG. 10 is intended to depict the representative major components of an exemplary computer system 1001. In some embodiments, however, individual components may have greater or lesser complexity than as represented in FIG. 10, components other than or in addition to those shown in FIG. 10 may be present, and the number, type, and configuration of such components may vary.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment currently known or that which may be later developed.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide, or other transmission media (e.g., light pulses passing through a fiber-optic cable) or electrical signals transmitted through a wire.

Computer readable program instructions described herein can be downloaded to respective computing/processing devices from a computer readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer, or entirely on a remote computer or server. In the latter scenario, the remote computer may be connected to the user's computer through any type of network, including a local area network (LAN) or a wide area network (WAN) or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions which comprises one or more executable instructions for implementing the specified logical function(s). In some alternative implementations, the functions noted in the blocks may occur out of the order noted in the figures. For example, two blocks shown in succession may, in fact, be accomplished as one step, executed concurrently, substantially concurrently, in a partially or wholly temporally overlapping manner, or the blocks may sometimes be executed in the reverse order depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present disclosure has been described in terms of specific embodiments, it is anticipated that alterations and modification thereof will become apparent to the skilled in the art. The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application, or the technical improvement over technologies found in the marketplace or to enable others of ordinary skill in the art to understand the embodiments disclosed herein. Therefore, it is intended that the following claims be interpreted as covering all such alterations and modifications as fall within the true spirit and scope of the disclosure.

What is claimed is:

1. A computer-implemented method of tracking infection, said method comprising:
acquiring situational data by a network architecture, wherein said network architecture is a virtual network function;
receiving, via a dedicated channel, participant data associated with a participant by said network architecture;

abstracting said participant data via said virtual network function;

accepting object data associated with an object by said network architecture;

calculating a viability time using weightage-based filtering;

generating a likelihood of infectiousness of said object based on said participant data, said object data, and said viability time;

generating an infection map with said virtual network function using said situational data, said abstracted participant data, and said likelihood of infectiousness of said object; and displaying said infection map to one or more users.

2. The computer-implemented method of claim 1 wherein said situational data includes viability data wherein said viability data includes duration of viability of at least one communicable pathogen on at least one surface type given at least one prescribed set of atmospheric conditions.

3. The computer-implemented method of claim 1 wherein said participant data includes a participant location and a participant health status, and wherein said object data includes an object location and an object composition.

4. The computer-implemented method of claim 3 further comprising:

determining whether said participant is in proximity of said object by cross-verifying said participant location with said object location.

5. The method of claim 4 wherein determining whether said participant is in proximity of said object by cross-verifying said participant location with said object location comprises:

comparing said participant location to said object location; and identifying, from said comparing, that said participant location and said object location are above a threshold proximity level.

6. The computer-implemented method of claim 3 further comprising:

updating said likelihood of infectiousness of said object and said location of said object over time.

7. The computer-implemented method of claim 1 further comprising:

generating a logical channel wherein said participant data is submitted to said network architecture via said logical channel.

8. The computer-implemented method of claim 1 wherein at least one of said participant data and said object data is collected from one or more internet of things devices.

9. A system that tracks infection, said system comprising:

a memory; and a processor in communication with said memory, said processor being configured to perform operations comprising:

acquiring situational data by a network architecture, wherein said network architecture is a virtual network function;

receiving, via a dedicated channel, participant data associated with a participant by said network architecture;

abstracting said participant data via said virtual network function;

accepting object data associated with an object by said network architecture;

calculating a viability time using weightage-based filtering;

generating a likelihood of infectiousness of said object based on said participant data, said object data, and said viability time;

generating an infection map with said virtual network function using said situational data, said abstracted participant data, and said likelihood of infectiousness of said object; and displaying said infection map to one or more users.

10. The system of claim 9 wherein said situational data includes viability data wherein said viability data includes duration of viability of at least one communicable pathogen on at least one surface type given at least one prescribed set of atmospheric conditions.

11. The system of claim 9 wherein said participant data includes a participant location and a participant health status, and wherein said object data includes an object location and an object composition, further comprising:

determining whether said participant is in proximity of said object by:

comparing the said participant location to said object location and identifying, from said comparing, that said participant location and said object location are above a threshold proximity level.

12. The system of claim 9 further comprising:

generating a logical channel wherein said participant data is submitted to said network architecture via said logical channel.

13. The system of claim 9 wherein at least one of said participant data and said object data is collected from one or more internet of things devices.

14. A computer program product for tracking infection, said computer program product comprising a computer readable storage medium having program instructions embodied therewith, said program instructions executable by a processor to cause said processor perform a function, said function comprising:

acquiring situational data by a network architecture, wherein said network architecture is a virtual network function;

receiving, via a dedicated channel, participant data associated with a participant by said network architecture;

abstracting said participant data via said virtual network function;

accepting object data associated with an object by said network architecture;

calculating a viability time using weightage-based filtering;

generating a likelihood of infectiousness of said object based on said participant data, said object data, and said viability time;

generating an infection map with said virtual network function using said situational data, said abstracted participant data, and said likelihood of infectiousness of said object; and displaying said infection map to one or more users.

15. The computer program product of claim 14 wherein said situational data includes viability data wherein said viability data includes duration of viability of at least one communicable pathogen on at least one surface type given at least one prescribed set of atmospheric conditions.

16. The computer program product of claim 14 wherein said participant data includes a participant location and a participant health status, and wherein said object data includes an object location and an object composition, further comprising:

determining whether said participant is in proximity of said object by:
  comparing the said participant location to said object location and
  identifying, from said comparing, that said participant location and said object location are above a threshold proximity level.

17. The computer program product of claim 14 wherein at least one of said participant data and said object data is collected from one or more internet of things devices.

* * * * *